United States Patent [19]

Regimand

[11] Patent Number: 4,766,319
[45] Date of Patent: Aug. 23, 1988

[54] PORTABLE NUCLEAR MOISTURE-DENSITY GAUGE WITH LOW ACTIVITY NUCLEAR SOURCES

[75] Inventor: Ali Regimand, Raleigh, N.C.

[73] Assignee: Troxler Electronic Laboratories, Inc., Research Triangle Park, N.C.

[21] Appl. No.: 13,678

[22] Filed: Feb. 12, 1987

[51] Int. Cl.$^4$ .................... G01N 23/22; G01N 23/222
[52] U.S. Cl. ....................................... 250/390; 250/391
[58] Field of Search ........... 250/390 D, 390 E, 390 C, 250/390 R, 308, 358.1, 270, 391

[56] References Cited

U.S. PATENT DOCUMENTS

| | | | |
|---|---|---|---|
| 2,781,453 | 2/1957 | Belcher et al. | 250/391 |
| 3,072,790 | 1/1963 | Hopkinson et al. | 250/270 |
| 3,544,793 | 12/1970 | Bless et al. | 378/54 |
| 4,028,267 | 6/1977 | Christell et al. | 250/308 |
| 4,152,600 | 5/1979 | Berry | 250/252.1 |
| 4,424,444 | 1/1984 | Smith, Jr. et al. | 250/270 |
| 4,525,854 | 6/1985 | Molbert et al. | 378/89 |
| 4,542,472 | 9/1985 | Toms | 364/556 |
| 4,581,599 | 4/1986 | Toms | 340/286 M |

FOREIGN PATENT DOCUMENTS 1168379  5/1984  Canada .................................. 250/270

OTHER PUBLICATIONS

Volarovich et al., "Use of the Neutron-Gamma Method to Determine the Bulk Density and Moisture of Peat", 5/1974, pp. 406–408.

Primary Examiner—Janice A. Howell
Assistant Examiner—William F. Rauchholz
Attorney, Agent, or Firm—Bell, Seltzer, Park & Gibson

[57] ABSTRACT

The nuclear moisture-density gauge of the present invention employs a low activity neutron radiation source and a low activity gamma radiation source. In order to achieve more accurate density measurements at the relatively low count rates which results from the use of a low activity gamma source, the present invention is provided with means for generating a correction signal which is a function of the moisture content of the test material and which represents the amount of gamma radiation emitted from the test material resulting from the neutron capture reaction due to the presence of neutron capture elements, such as hydrogen, present in the test material. This correction signal is applied to the uncorrected density signal obtained from the gauge to thereby obtain a corrected density measurement which is unaffected by background gamma radiation caused by the presence of neutron capture elements in the test material. The gauge is also provided with means for correcting naturally occurring background gamma radiation from the test material.

10 Claims, 2 Drawing Sheets

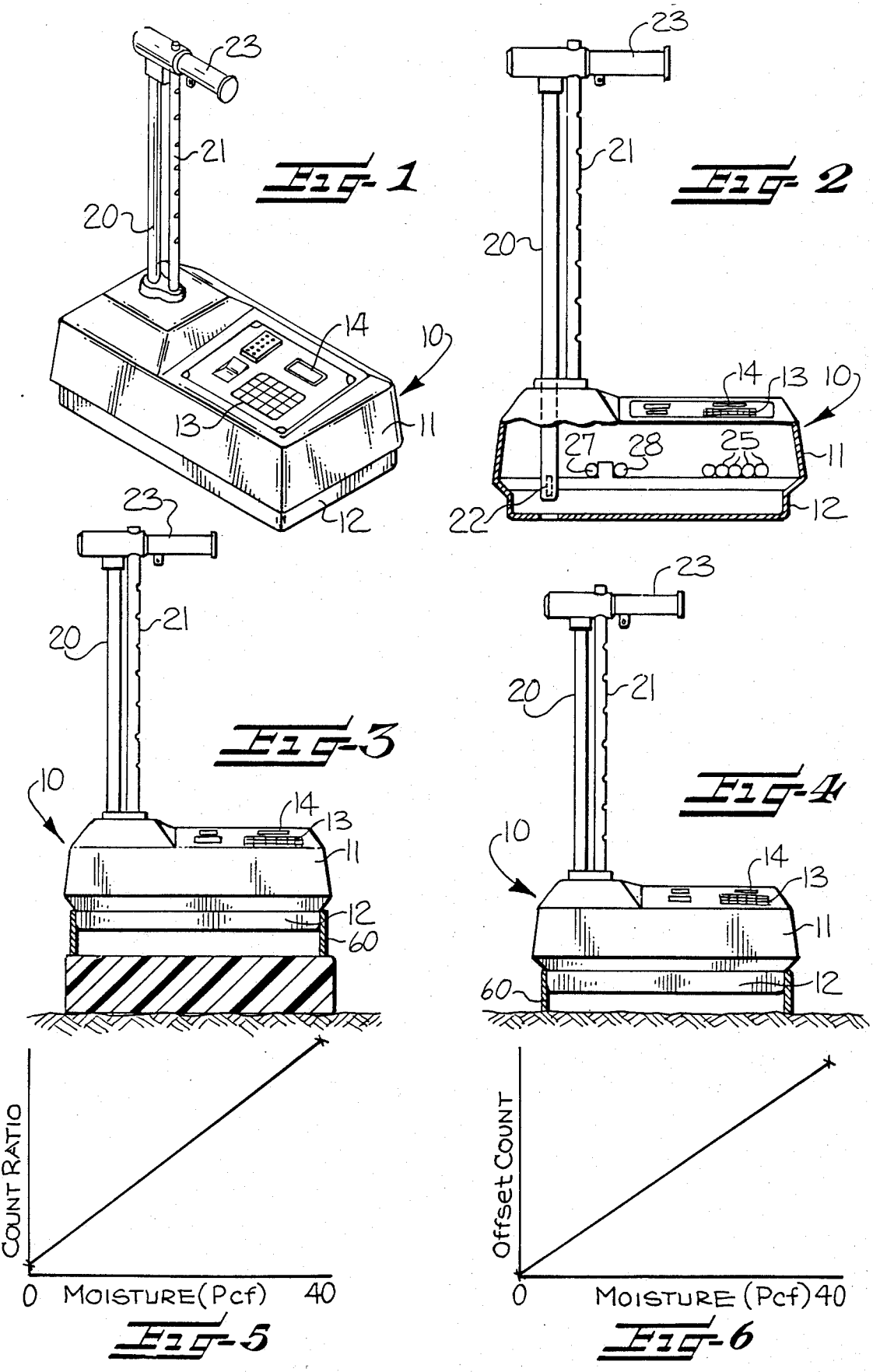

PORTABLE NUCLEAR MOISTURE-DENSITY GAUGE WITH LOW ACTIVITY NUCLEAR SOURCES

FIELD AND BACKGROUND OF THE INVENTION

This invention relates to a portable test instrument, and more particularly to a nuclear gauge for measuring the moisture and density properties of a test material.

Portable nuclear gauges are frequently used in the construction industry for measuring the moisture content and density of soils, soil-stone aggregates, cement, and asphalt. One such gauge which has been commercially available for a number of years is the 3400 Series Surface Moisture-Density Gauge manufactured by Troxler Electronic Laboratories of Research Triangle Park, N.C., the assignee of the present invention.

These gauges utilize the principle of Compton scattering of gamma rays for determining the density characteristics of the test material. The moisture content of the test material is determined by using a neutron source and detecting neutrons which are thermalized by the hydrogen in water present in the test material. Portable test instruments employing these principles are disclosed for example in U.S. Pat. Nos. 3,544,793, 4,525,854, 4,542,472, 4,581,599, and 2,781,453.

The aforementioned type of gauge typically employs nuclear sources having an activity level in the millicurie range. For example, the Troxler 3400 Series moisture-density gauge employs a cesium-137 gamma source containing approximately eight millicurie of cesium-137. The neutron source is a mixture of americium oxide and beryllium metal containing about 40 millicurie of americium-241. Although the quantities of radioactive material contained in these gauges are quite small, and an operator may safely use such a gauge daily without receiving any bodily damage due to radiation, nonetheless, precautions and care should be followed in the operating and handling of such gauges.

Some jurisdictions impose severe restrictions on the activity of the nuclear sources which may be used in nuclear test instruments, and consequently, moisture-density gauges of the type described above cannot be used in such jurisdictions. For example, in Japan the maximum limit for radiation sources is below 100 microcuries. Even in jurisdictions where higher limits are permitted, nuclear instruments are often subject to cumbersome regulations and licensing requirements.

In order to overcome the aforementioned disadvantages and limitations, nuclear moisture-density gauges have been proposed which use nuclear sources of relatively low activity, e.g. in the microcurie range. Gauges employing these low activity nuclear sources are subject to fewer and less stringent restrictions and regulations. However, such gauges have been shown to have relatively low levels of accuracy, which seriously limits their usefulness in commercial applicatios. More specifically, because of the low activity nuclear sources, the count rates are significantly lower and as a consequence, extraneous background radiation imparts significantly higher error than if higher activity sources with higher counting rates were employed.

With the foregoing in mind, it is an important object of the present invention to provide a nuclear moisture-density gauge which uses a low activity nuclear source and which provides significantly better accuracy than heretofore provided.

SUMMARY OF THE INVENTION

The nuclear moisture-density gauge of the present invention employs a low activity neutron radiation source for emitting fast neutrons into the test material, a thermal neutron detector for detecting thermal neutrons which have been moderated by neutron moderating elements, such as hydrogen, present in the test material and for generating a signal representative of the moisture content of the test material, a low activity gamma radiation source for emitting gamma radiation into the test material, and a gamma radiation detector for detecting gamma radiation which is emitted from the source and which passes through the test material, the quantity of such radiation being related to the density of the test material.

As noted earlier, because of the low activity nuclear sources employed, the radiation counts obtained by the detectors are significantly lower, and consequently, background radiation from naturally occurring radioactive elements present in the test material have a significantly greater effect on the overall count. To eliminate the error contributed by naturally occurring background radiation, a background count is taken using a reference standard block. Two measurements are taken using a predetermined air gap, e.g. 1.5 inch, under the gauge, one reading being taken 1.5 inch above the test material and another reading taken 1.5 inch above a reference standard block, such as polyethylene block, capable of shielding the gauge from any natural background radiation emanating from the test material. The difference in the two count rates is attributable to naturally occurring background radiation from the test material. This difference is then used as a correction factor to correct for naturally occurring background radiation in subsequent test readings.

It has also been discovered in accordance with the present invention that in addition to naturally occurring background radiation, a very significant source of error in density measurement is due to neutron capture elements present in the test material. More particularly, this error is due to the absorption of thermal neutrons in the test material by certain elements, such as the hydrogen in water, present in the test material, which have a relatively large neutron capture crosssection, hereinafter referred to as neutron capture elements. Since the mass of hydrogen is close to the mass of a neutron, hydrogen quite readily interacts with neutrons, in some instances scattering or thermalizing the neutron, while in other instances completely capturing the neutron. When neutrons emitted into the test material from the neutron source in the gauge are captured and absorbed, gamma rays are ejected. This is called the thermal neutron capture reaction and is commonly denoted by (n, $\gamma$) where n stands for neutron and $\gamma$ for the capture gamma rays produced in this reaction. While the thermal neutron capture reaction is a well known principle of nuclear physics, the existence of capture gamma radiation has not heretofore been considered as a source of error in making nuclear density measurements.

The present invention is based upon the recognition and discovery that in a low activity nuclear moisture-density gauge, the capture gamma rays which are produced during a measurement due to the presence of neutron capture elements in the test material contribute significantly to the total gamma count and unless corrective action is taken, the capture gamma radiation introduces significant error into the density reading.

In accordance with the present invention a nuclear moisture-density gauge employing a low activity gamma radiation source and a low activity neutron source is provided with means for generating a correction signal which is a function of the moisture content of the test material and which represents the amount of gamma radiation emitted from the test material resulting from the (n, γ) neutron capture reaction due to the presence of neutron capture elements, such as hydrogen, in the test material. This correction signal is applied to the uncorrected density signal obtained from the gauge to thereby obtain a corrected density measurement which is unaffected by background gamma radiation caused by the presence of neutron capture elements in the test material.

Thus, the present invention, in one aspect, provides a method of measuring the density of a test material using a low activity gamma radiation source in the presence of a neutron radiation source, comprising:

directing fast neutrons from a neutron radiation source into the test material, detecting neutrons which have been moderated and thermalized by neutron moderating elements present in the test material and generating a signal representative of the moisture content of the test material, directing gamma radiation from a gamma radiation source into the test material, detecting gamma radiation emitted from the source and which passes through the test material and generating an uncorrected signal which is representative of the density of the test material plus error due to extraneous background radiation, generating a correction signal which is function of said moisture signal and which represents the amount of gamma radiation emitted from said test material resulting from the (n, γ) neutron capture reaction due to the presence of neutron capture elements, such as hydrogen, in the test material, and applying said correction signal to said uncorrected density signal to obtain a corrected density signal which is unaffected by background gamma radiation caused by the presence of neutron capture elements in the test material.

In another aspect, the present invention provides a portable low activity nuclear measuring gauge for measuring the density and moisture characteristics of a test material, comprising a low activity neutron radiation source for emitting fast neutrons into the test material, thermal neutron detector means mounted in predetermined spaced relationship to said neutron source for detecting thermal neutrons which have been moderated by neutron moderating elements, such as hydrogen, present in the test material and for generating a signal representative of the moisture content of the test material, a low activity gamma radiation source for emitting gamma radiation into the test material, gamma radiation detector means mounted in predetermined spaced relationship to said gamma radiation source for detecting gamma radiation which is emitted from the source and which passes through the test material and for generating an uncorrected signal which is representative of the density of the test material plus error due to extraneous background radiation, means operatively connected to said thermal neutron detector means for generating a correction signal which is a function of said moisture signal and which represents the amount of gamma radiation emitted from said test material resulting from the (n, γ) neutron capture reaction due to the presence of neutron capture elements, such as hydrogen, in the test material; and means for applying said correction signal to said uncorrected density signal to obtain a corrected density signal which is unaffected by background gamma radiation caused by the presence of neutron capture elements, such as hydrogen, in the test material.

BRIEF DESCRIPTION OF THE DRAWINGS

Some of the features and advantages of the invention having been described, others will become apparent from the detailed description which follows and from the accompanying drawings in which FIG. 1 is a perspective view of a nuclear moisture-density gauge in accordance with the present invention;

FIG. 2 is a cross-sectional view thereof;

FIG. 3 is a side elevational view of the gauge illustrating a part of the calibration procedure in which a measurement is taken through a predetermined air gap and into a reference standard block;

FIG. 4 is a view similar to FIG. 3 showing a reference count being taken through an air gap into the underlying test material;

FIGS. 5 and 6 are graphs used in the calibration and correction procedures of the present invention;

DESCRIPTION OF THE ILLUSTRATED EMBODIMENT

Figure 7:
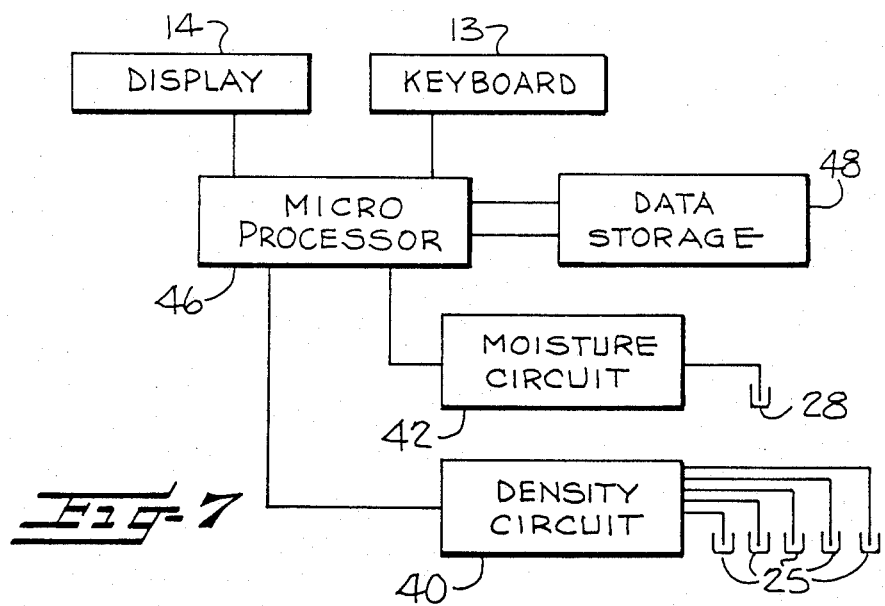
FIG. 7 is a schematic diagram of the electronic components of the gauge.

While the present invention will be described hereinafter with particular reference to the accompanying drawings, it is to be understood at the outset that it is contemplated that the present invention may be varied in specific detail from that illustrated and described herein while still achieving the desirable characteristics and features of the present invention. Accordingly, the description which follows is intended to be understood as a broad enabling disclosure directed to persons skilled in the applicable arts, and is not to be understood as being restrictive.

Referring now more particularly to the drawings, the gauge illustrated includes a housing, generally indicated at 10 including an upper section 11 and a lower section 12 formed of a suitable lightweight material, such as cast aluminum. The lower section 12 has a relatively flat bottom surface so that the gauge can be positioned directly upon the test material which is to be measured. On the upper side of the housing, a keyboard 13 is provided by which an operator can control the various functions of the gauge and a display 14, such as a liquid crystal display, is provided for communicating measurement readings and other information to the operator.

A source rod 20 extends vertically through the housing 10 and upwardly from a supporting column 21 on the upper side of the housing. A low activity gamma source 22 (FIG. 2) is mounted in the lower end of the source rod 20. The low activity gamma source has an activity less than 1000 microcuries, preferably no more than 500 microcuries, and most desirably no more than about 100 microcuries. For example, a preferred low activity gamma source for use in the present invention is cobalt-60, having an activity of about 60 microcuries. The source rod 20 is mounted for vertical sliding movement between an upwardly retracted position as illustrated in FIG. 1 and any of several lowered positions, in which the lower end of the rod is either flush with the base for backscatter density measurements or protrudes downwardly below the lower surface of the housing for use in direct transmission density measurements. A handle 23 is mounted at the upper end of the source rod 20 to facilitate carrying the gauge and for positioning the source rod 20 at various preselected depth positions.

Geiger-Muller detector tubes 25 (FIG. 2) are located within the housing in a predetermined geometrical relationship with respect to the gamma source for detecting gamma radiation which is emitted from the source and which passes through the test material in reaching the detector tubes. From the detector tubes 25, an uncorrected signal, in the form of a total count per unit time is obtained. This uncorrected signal is representative of the density of the test material plus error due to extraneous background radiation, namely, naturally occurring background radiation and capture gamma radiation. As is explained more fully hereinafter, the present invention provides for generating correction signals to be applied to the uncorrected density signal to remove the error caused by such extraneous background radiation.

Located inside the housing 10 is a low activity neutron source 27 for use in obtaining the moisture measurement. The neutron source has an activity of less than 1000 microcuries, preferably no more than 500 microcuries, and most desirably no more than about 100 microcuries. For example, a preferred low activity neutron source for use in the present invention is Californium-252 having an activity of 30 microcuries. Thus, a gauge with the preferred low activity gamma source and the preferred low activity neutron source has a total activity of less than 100 microcuries. A thermal neutron detector tube 28, such as a He-3 tube, is mounted within the housing in spaced relationship to the neutron source 27 for detecting thermal neutrons which have been moderated by neutron moderating elements, such as hydrogen, present in the test material and for generating a signal which is representative of the moisture content of the test material.

The electronic components of the gauge, indicated schematically in FIG. 7, include a density measuring circuit 40 connected to the Geiger-Muller tubes 25 and a moisture measuring circuit 42 connected to the thermal neutron detector 28. The density measuring circuit 40 and the moisture measuring circuit 42 contains amplifiers, threshold detectors and logic units for accepting pulses from the Geiger-Muller tubes 25 and thermal neutron detector 28 and supplying count pulses to a microprocessor 46 having an associated memory device 48, such as a random access memory (RAM) and/or read only memory (ROM). The microprocessor 46 and associated memory device 48 function as the control processing element, and include a stored set of instructions which, through operator control, can be executed for carrying out density and/or moisture measurements on a test material. These electronic components are well known and have been widely used heretofore in nuclear moisture-density gauges. Accordingly, a further, more detailed explanation of these components is not deemed warranted.

Similarly, the theoretical principles utilized in making moisture and density measurements, as well as the procedures and computations employed are similar to those heretofore widely used with higher activity nuclear gauges. Persons skilled in this art who are familiar with such gauges will therefore have a complete appreciation and understanding of how the gauge of the present invention operates. Accordingly, the description which follows will be directed primarily to the significant differences in the function and operation of the moisture-density gauge of the present invention over prior conventional gauges.

With respect to density measurement, a primary difference over prior methods of density measurement and the computation techniques employed involves correcting for the capture gamma radiation caused by the presence of neutron absorbing elements in the test material and the resulting neutron capture reaction which releases gamma radiation. A further difference correcting for natural background radiation from the test material.

Whenever a density measurement is taken in accordance with the present invention, a measurement is also taken of the moisture present in the test material. Knowing the moisture present in the test material, the quantity of gamma radiation produced by the neutron capture reaction due to the presence of hydrogen in the test material can be determined, and this is applied as a correction factor to eliminate from the density reading the gamma counts attributable to the neutron capture reaction.

To determine the correction factor to be applied to the density reading to correct for capture gamma radiation a preliminary calibration/correction procedure is followed in which several air gap measurements are made with the gauge. An air gap distance of about 1.5 inch has been found to be suitable in practice. As illustrated in FIGS. 3 and 4, a rectangular collar 60 is supplied with the gauge, with the dimensions of the rectangular collar corresponding to the dimensions of the lower section 12 of the gauge housing. By placing the gauge housing on the collar 60, the gauge can be held a predetermined distance, e.g. 1.5 inch, above the underlying substrate for taking the calibration readings.

Initially, moisture and density readings are taken through the 1.5 inch air gap on two calibration blocks of different moisture content. For example, one reading on a magnesium block of zero moisture and another reading on a magnesium/polyethylene laminated standard of known moisture content (e.g. 40 pounds per cubic foot). Commonly owned U.S. Pat. No. 4,152,600 describes a suitable moisture gauge calibration standard which may be employed for this purpose. The two density counts, DC1 and DC2, and two moisture counts MC1 and MC2 are recorded. Divide MC1 and MC2 by the moisture standard count taken on top of the reference standard block (e.g. a 3.5 inch polyethylene standard block) and use these count ratios to calibrate the gauge in the 1.5 inch gap mode for moisture. This may be accomplished by fitting a straight line to the data points, as indicated in FIG. 5. By using the graph of FIG. 5, or a suitable equation defining this relationship, the moisture content of a test specimen can be readily determined from the moisture count ratio.

With a 1.5 inch air gap beneath the gauge, the density counts should be independent of the density of the test material underlying the collar. In other words, the density counts should be the counts from the air in the 1.5 inch air gap and the gammas going directly from the source to the detectors. Therefore, any change in the apparent density counts between DC1 and DC2 may be assumed to be due to neutron absorption and thus an emission of gamma particles that are detected by the Geiger-Muller tubes. It is thus possible to obtain an offset count or correction factor for any given moisture content. In our example, there is no moisture background error introduced by the magnesium (zero moisture) block, since there is no hydrogen present in this material. Therefore, at moisture=0, offset count=0
at moisture=40, offset count=DC 2−DC1.

Then another straight line relationship can be established to produce the graph illustrated in FIG. 6. By using the graph shown in FIG. 6, or a suitable mathematical equation defining this relationship, it is possible to generate for any given moisture content, the appropriate offset count or correction factor to account for the gamma particles produced by neutron absorption by the hydrogen present in the test sample. Thus, for example, the correction factor relationship may be defined by a simple equation $$\text{offset count} = Y_1 + Y_2 M_1$$

where
$Y_1$ and $Y_2$ are constants
$M_1$ is moisture content.

The thus obtained offset count is subtracted from the experimentally measured density count to obtain a count which is corrected for moisture background.

It is also desirable to correct the experimentally measured density count for background radiation from naturally occurring radiation in the test material. A correction factor for the naturally occurring background radiation may be determined by taking a background count using a reference standard block. Two measurements are taken using a predetermined air gap, one reading being taken 1.5 inch above the test material as shown in FIG. 4 and the other reading being taken 1.5 inch above the reference block as shown in FIG. 3. The difference in the two count rates is attributable to naturally occurring radiation from the test material and is used as a correction factor for natural background radiation in subsequent test readings.

In practice, the moisture and density measurement calculations are carried out by the microprocessor using a set of stored calibration constants, including sets of factory determined density and moisture calibration constants. Constants defining the moisture background correction factor and the naturally occurring background radiation are also stored, and utilized by the microprocessor in carrying out the moisture and density calculations. Also, in practice the correction for natural background radiation and the correction for background due to neutron capture are most conveniently carried out simultaneously rather than separately.

Figure 8:
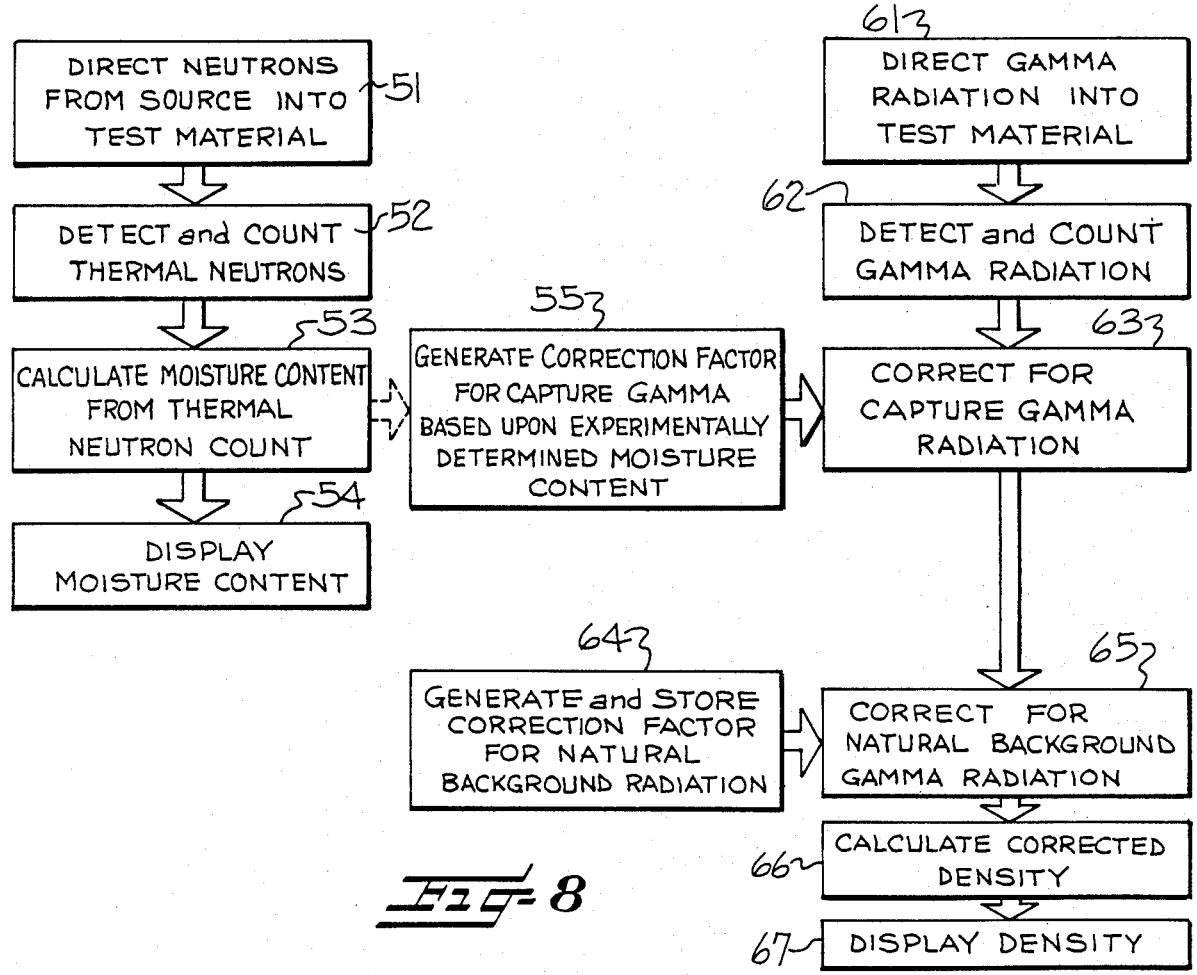
FIG. 8 is a schematic flow diagram illustrating the procedures employed in obtaining a moisture and density measurement in accordance with the invention.

The procedures employed are illustrated by the flow diagram of FIG. 8. During a test measurement, a moisture count is taken by directing neutrons from the source 27 into the test material and counting for a predetermined period of time, the thermal neutrons detected by detector 28, as represented at (51) and (52). The moisture content is calculated from the thermal neutron count, and the results are displayed on the display device 14, as represented at 53 and 54. At the same time, a density count is taken by directing gamma radiation from the source 22 and counting gamma radiation detected by the detector tubes 25, as represented at (61) and (62). The moisture content determined at (53) is utilized to generate a correction factor to account for background capture gamma radiation (55) and this correction factor is applied to the gamma count (63). A correction factor for background radiation is generated as previously described (64) and is also applied to the gamma count (65) to produce a corrected density reading (66) which, in turn, is displayed on the display device 14 (67).

That which I claim is:

1. A portable low activity nuclear measuring gauge for measuring the density and moisture characteristics of a test material, comprising
   a low activity neutron radiation source for emitting fast neutrons into the test material,
   thermal neutron detector means mounted in predetermined spaced relationship to said neutron source for detecting thermal neutrons which have been moderated by neutron moderating elements, such as hydrogen, present in the test material and for generating a signal representative of the moisture content of the test material,
   a low activity gamma radiation source for emitting gamma radiation into the test material,
   gamma radiation detector means mounted in predetermined spaced relationship to said gamma radiation source for detecting gamma radiation which is emitted from the gamma radiation source and which passes through the test material and for generating an uncorrected signal which is representative of the density of the test material plus error due to extraneous background radiation,
   means operatively connected to said thermal neutron detector means for generating a correction signal which is a function of said moisture signal and which represents the amount of gamma radiation emitted from said test material resulting from the (n, γ) neutron capture reaction due to the presence of neutron capture elements, such as hydrogen, in the test material; and
   means for applying said correction signal to said uncorrected density signal to obtain a corrected density signal which is unaffected by background gamma radiation caused by the presence of neutron capture elements, such as hydrogen, in the test material.

2. A gauge according to claim 1 wherein said neutron radiation source has a radiation activity of less than 1000 microcuries.

3. A gauge according to claim 1 wherein said gamma radiation source has a radiation activity of less than 1000 microcuries.

4. A gauge according to claim 1 wherein said gamma radiation source and said neutron radiation source have a total radiation activity of no more than 100 microcuries.

5. A gauge according to claim 1 additionally including means for receiving and storing a second correction signal representative of natural background radiation present in the test material, and wherein said means for applying said correction signal to said density signal is also operable for applying said second correction signal to said density signal to thereby obtain a corrected density signal which is unaffected both by natural background radiation present in the test material and by background gamma radiation caused by the presence of neutron capture elements in the test material.

6. A method of measuring the density of a test material using a low activity gamma radiation source in the presence of a neutron radiation source, comprising:
    directing fast neutrons from a neutron radiation source into the test material,
    detecting neutrons which have been moderated and thermalized by neutron moderating elements present in the test material and generating a signal representative of the moisture content of the test material,
    directing gamma radiation from a gamma radiation source into the test material,
    detecting gamma radiation emitted form the gamma radiation source and which passes through the test material and generating an uncorrected signal which is representative of the density of the test material plus error due to extraneous background radiation,
    generating a correction signal which is a function of said moisture signal and which represents the amount of gamma radiation emitted from said test material resulting from the (n, $\gamma$) neutron capture reaction due to the presence of neutron capture elements, such as hydrogen, in the test material, and
    applying said correction signal to said uncorrected density signal to obtain a corrected density signal which is unaffected by background gamma radiation caused by the presence of neutron capture elements in the test material.

7. A method according to claim 6 additionally including providing a second correction signal representative of natural background radiation present in the test material, and also applying said second correction signal to said uncorrected density signal to obtain a corrected density signal which is unaffected by both the natural background radiation present in the test material and by background gamma radiation caused by the presence of neutron capture elements in the test material.

8. A method according to claim 6 wherein said step of directing fast neutrons comprises directing neutrons from a low activity neutron source having a radiation activity of less than 1000 microcuries.

9. A method according to claim 6 wherein said step of directing gamma radiation comprises directing gamma radiation from a low activity gamma radiation source having a radiation activity of less than 1000 microcuries.

10. A method according to claim 6 wherein the neutrons and the gamma radiation are directed from radiation sources having a total radiation activity of no more than 100 microcuries.

* * * * *

UNITED STATES PATENT AND TRADEMARK OFFICE
CERTIFICATE OF CORRECTION

PATENT NO. : 4,766,319

DATED : August 23, 1988

INVENTOR(S) : Ali Regimand

It is certified that error appears in the above-identified patent and that said Letters Patent is hereby corrected as shown below:

Column 1, line 60, "applicatios" should be -- applications --.

Column 9, line 16, "form" should be -- from --.

Signed and Sealed this

Seventeenth Day of January, 1989

Attest:

DONALD J. QUIGG

*Attesting Officer*      *Commissioner of Patents and Trademarks*